United States Patent [19]
Barnett et al.

[11] 3,960,000
[45] June 1, 1976

[54] FLIGHT SIMULATOR FOR MISSILES

[75] Inventors: Charles W. H. Barnett, Falls Church, Va.; George K. Lucey, Jr., Greenbelt, Md.; Douglas R. Augustine, Virginia Beach, Va.

[73] Assignee: The United States of America as represented by the Secretary of the Army, Washington, D.C.

[22] Filed: Nov. 8, 1974

[21] Appl. No.: 522,166

[52] U.S. Cl. .................................. 73/15.4; 73/147; 73/167
[51] Int. Cl.² .................................. G01N 25/00
[58] Field of Search ........ 73/15.4, 86, 147, 432 SD, 73/167

[56] References Cited
UNITED STATES PATENTS
3,709,026  1/1973  Rhodes et al. ................. 73/432 SD OTHER PUBLICATIONS
Kubiceck, Instruments & Control Systems, Mar. 1961, pp. 463–465.

*Primary Examiner*—S. Clement Swisher
*Attorney, Agent, or Firm*—Nathan Edelberg; Robert P. Gibson; Saul Elbaum

[57] ABSTRACT

Disclosed is a flight simulator for missiles. The system comprises means for directing heat toward the nose cone of a missile while simultaneously imparting axial rotation to the missile. Both the heat and the axial rotation are programmed to conform to actual inflight heat and spin conditions and the cycle of simultaneous heat and rotation is programmed to conform to such inflight conditions. Means are also provided for monitoring the proper fuse function at any given time during the simulated flight and for recording the entire cycle of simulated flight. The programmer can be programmed for the full real flight time of a missile such that the time-speed relationship can be matched to that of any real or proposed flight.

3 Claims, 1 Drawing Figure

U.S. Patent   June 1, 1976   3,960,000
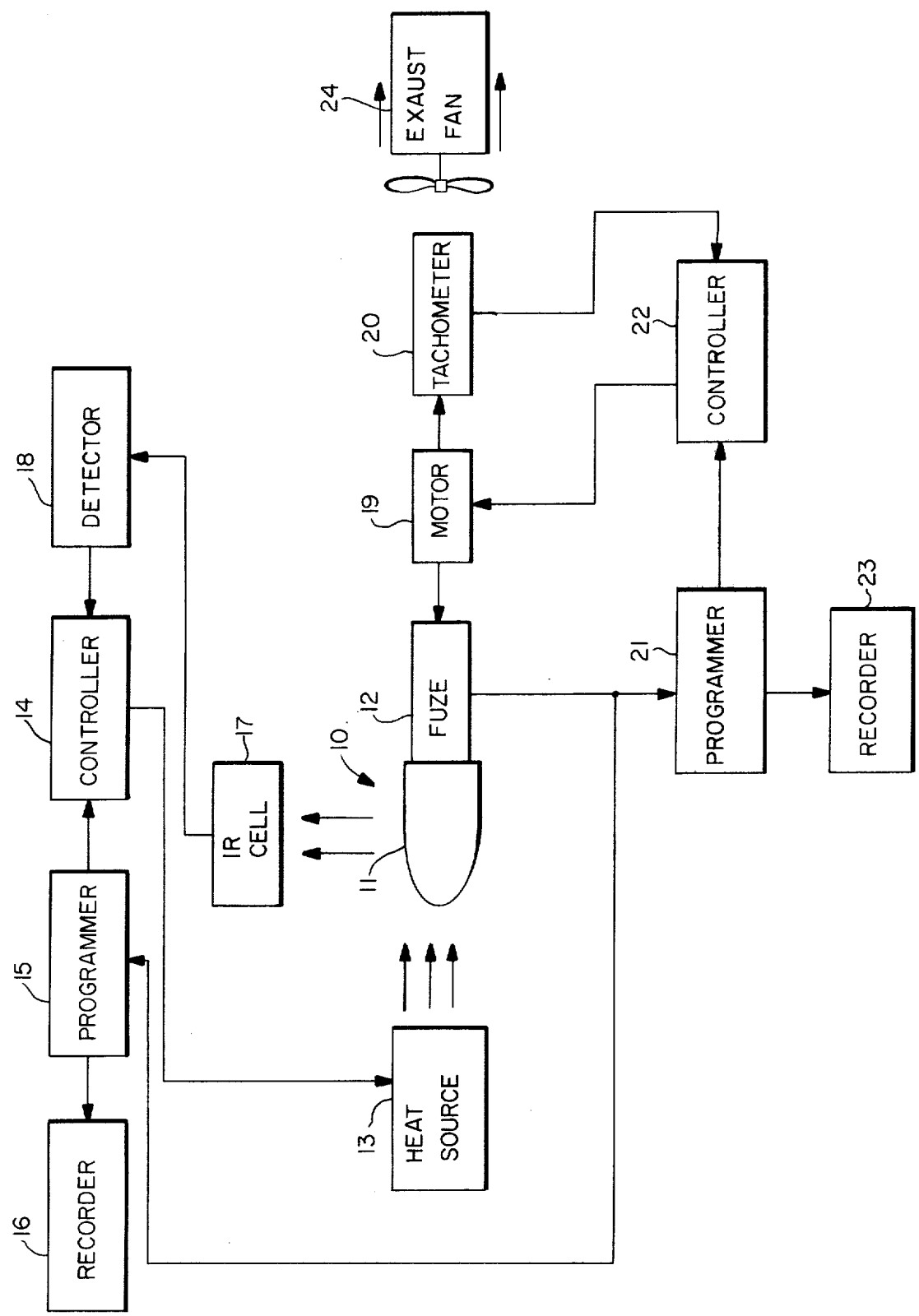

3,960,000

FLIGHT SIMULATOR FOR MISSILES

BACKGROUND OF THE INVENTION

This invention relates generally to a flight simulator and more specifically to a system for applying simultaneous heat and spin to a missile so as to simulate actual inflight conditions.

To the present day designs of missiles and artillery shells there exists the problem of fabricating a suitable leading element, the co-called nose cone. These nose cones are required to have a wide variety of characteristics which will enable them to function properly in an environment which can, at times, be quite hostile. Among these conditions are extremes of temperature, abrasive elements, mechanical shock and storage in other than ideal conditions. In addition, these nose cones are required to possess certain inherent qualities which will enable them to perform their required functions. Among these qualities are certain specified dielectric constants, mechanical strength, resistance to cracking, abrasion and heat defects.

The testing of these nose cones as well as the electronic fuse components contained therein, both in the laboratory and on the production line, has produced a wide variety of methods many of which have serious drawbacks and disadvantages. Among the most common and frequently used techniques of missile testing is that of launching and recovery of the missile with subsequent examination. A modified version of this method is that of propelling the missile on a carrier along a guided track and thereafter examining the missile. Another technique employs the facilities of a wind tunnel to simulate flight.

In none of the above cases is it possible to create a programmed, repeatable simulate flight conditions such as is the case with the present invention.

It is, therefore, a primary object of this invention to provide a flight simulator for missiles.

A more particular object of the invention is to provide a programmed flight simulator capable of repetition.

Still another object of the invention is to provide a programmed flight simulator capable of indefinite storage in permanent form for future reuse.

An additional object is to provide a flight simulator capable of reproducing actual flight conditions or theoretical flight conditions as desired.

Yet an additional object of the invention is to provide a flight simulator capable of visual instantaneous observation at any given time during the simulated flight path.

Still a further object of the invention is to provide a flight simulator capable of testing the proper fuse function at any given time during the simulated flight path.

These and other objects of the invention will become more apparent with reference to the appended claims and to the accompanying drawings in which the attached FIGURE illustrates one embodiment of the present invention.

SUMMARY OF THE INVENTION

Briefly, in accordance with this invention, a flight simulator for missiles is provided. The simulator comprises a means for directing heat toward the nose cone of a missile and for controlling the application of such heat so as to conform to in-flight heating conditions. Additionally, means are provided for imparting axial rotation to the missile simultaneously with the application of heat. Again, the rotation is controlled by a programmer so as to conform to in-flight heating conditions. Finally, means are provided for programming the cycle of simultaneous heat and rotation to conform to in-flight conditions. The correct fuse function at any given point during the simulated flight can also be monitored and the entire program of heat and spin is automatically provided at the output of a visual recorder. Feedback means are provided to ensure that both the heat and spin functions are maintained within predetermined limits of deviation.

DESCRIPTION OF THE PREFERRED EMBODIMENT

Referring now to the FIGURE, there is shown a missile 10 having a nose cone 11 and a fuze body 12. The missile 10 is mounted so as to undergo axial rotation by means of an electric motor 19 which is controlled by controller 22. Programmer 21 actuates controller 22 so as to apply the appropriate rate and time-speed relationship of spin to missile 10. The output of programmer 21 is visually recorded by recorder 23. A tachometer 20 monitors the instantaneous speed of motor 19 and provides a feedback signal to controller 22 so as to maintain the predetermined speed of motor 19 within its specified limits of deviation.

Simultaneously with the application of axial rotation to missile 10, nose cone 11 is subjected to intense heat from heat source 13. This heat source may typically take the form of an oxygen gas flame which is controlled by controller 14. Again, the programmer 15 actuates controller 14 so as to provide the appropriate degree of heat at any given time during the simulated flight path. An IR cell 17 monitors the actual heat at the surface of nose cone 11 and provides a feedback signal through detector 18 to controller 14 so as to maintain the desired heat level within specified limits of deviation. Again, the entire program is available for observation by means of recorder 16. Exhaust fan means 24 is provided to quickly remove heated air so as to facilitate the rapid changes of heat conditions which may be required during simulated flight. The entire system is designed to take advantage of well known and presently available off the shelf electronic components. Once properly programmed for the appropriate heat and spin conditions, the system can adequately simulate and match the conditions that such a missile would encounter in actual flight after initial set-back and before impact with the target.

An anechoic chamber may be placed around the missile to simulate free space conditions. In this case, the target can be introduced into the RF field of a proximity fuse at any time during the flight for purposes of testing the fuse functioning. The device is capable of being operated by one person and a high rate of repetition of tests is possible.

It should be understood that the inventors do not desire to be limited to the exact details of construction shown and described, for obvious modifications can be made by a person skilled in the art.

We claim as our invention:

1. A flight simulator for missiles having a nose cone and a fuse body comprising: means for directing heat towards the nose cone of said missile; means for monitoring the temperature of said nose cone and providing a feedback signal to adjust the application of said heat to the desired level; means for imparting axial rotation to said missile simultaneously with the application of said heat; means for monitoring the spin rate of said fuse and providing a feedback signal to adjust the application of said rotation to the desired level; means for programming the cycle of simultaneous heat and rotation to conform to in-flight conditions; and means for monitoring the fuse function at any given time during the simulated flight.

2. The invention defined in claim 1 further comprising means for recording the cycle of heat and rotation during the simulated flight.

3. The invention defined in claim 1 further comprising means for exhausting heated air in the vicinity of the nose cone to facilitate rapid changes of heat conditions.

* * * * *